United States Patent [19]  [11] 4,354,114
Karnaukhov et al.  [45] Oct. 12, 1982

[54] APPARATUS FOR INVESTIGATION OF FLUORESCENCE CHARACTERISTICS OF MICROSCOPIC OBJECTS

[76] Inventors: Valery N. Karnaukhov, mikroraion "AB", dom 7, kv. 67; Valery A. Yashin, mikroraion "AB", dom 6, kv. 100; Vladimir I. Kulakov, mikroraion "V", dom 26, kv. 30; Vasily M. Vershinin, mikroraion "AB", dom 3, kv. 52; Vladimir V. Dudarev, mikroraion "G", dom 26, kv. 75, all of Puschino Moskovskoi oblasti, U.S.S.R.

[21] Appl. No.: 82,809

[22] Filed: Oct. 9, 1979

[51] Int. Cl.$^3$ .................... G01N 21/38; G01J 1/58
[52] U.S. Cl. .................... 250/458.1; 250/461.2; 356/39
[58] Field of Search ............... 250/461 B, 461 R, 459, 250/372, 458; 356/317, 318, 39; 340/146.3 CA

[56] References Cited

U.S. PATENT DOCUMENTS

| | | | |
|---|---|---|---|
| 3,413,464 | 11/1968 | Kamentsky | 250/461 B |
| 3,503,684 | 3/1970 | Preston, Jr. et al. | 356/39 |
| 3,684,377 | 8/1972 | Adams et al. | 250/461 B |
| 3,883,247 | 5/1975 | Adams | 250/461 B |
| 3,916,197 | 10/1975 | Fulwyler | 250/461 B |
| 3,916,205 | 10/1975 | Kleinerman | 250/461 B |
| 4,125,828 | 11/1978 | Resnick et al. | 356/39 |

FOREIGN PATENT DOCUMENTS 78637 1/1950 U.S.S.R. .

OTHER PUBLICATIONS

"How to Choose an Automated Differential Counter", brochure, Geometric Data Corp., Wayne, Pa., undated.
Yakubovsky (ed.), "Analog & Digital Integrated Circuits", *Sovetskoe Radio*, Moscow, 1979, pp. 239–240.
Papyak et al. "Dual–Beam Pulse, Digital Microfluorimeter", *Cytology*, 16 (3), 1974, Navka Pub. House, Leningrad, pp. 395–396.
Olson, "Rapid Scanning Microspectrofluorimeter", *Rev. Sci. Inst.*, 31 (8), Aug. 1960, pp. 844–849.
"How to Buy a Differential Counter", brochure, Geometric Data Corp., Wayne, Pa., undated.
Stovel et al., "Individual Cell Sorting", *J. Histochem. Cytochem.*, 27 (1), 1979, pp. 284–288.
Frank et al., "Spectral Characteristics of Acridine Orange Fluorochromated Cells of Human White Blood", *Biophysics, USSR Acad. Sciences*, vol. 22, 1977, Moscow, pp. 1016–2021.
Karnavkhov, "Fluorescence Spectral Analysis of a Cell", *Theo. & Appl. Biophysics*, Navka Pub. House, Moscow, 1978, pp. 77–79.
Connelly (ed.), "Analog Integrated Circuits: Devices, Circuits, Systems & Applications", *Mir. Pub. House*, Moscow, 1977, pp. 152–154.
Schildkraut et al., "A System for Storage & Retrieval of Individual Cells Following Flow Cytometry", *J. Histochem. Cytochem.*, 27 (1), 1979, pp. 289–292.
Merrill et al., "Investigations in High-Precision Sorting", *J. Histochem. Cytochem.*, 27 (1), 1979, pp. 280–283.
Kachel et al, "Fast Imaging in Flow: A Means of Combining Flow-Cytometry & Image Analysis", *J. Histochem. Cytochem.*, 27 (1), 1979, pp. 335–341.
Kay et al., "Imaging in Flow", *J. Histochem. Cytochem.*, 27 (1), 1979, pp. 329–334.
Biophysics–USSR Academy of Science #UDC577.37, Franks et al. Spectral Characteristics of Cells, etc.–with translation.
Optical & Mechanical Eng. 1967, #9, Brumberg et al. Two Wave Micro Fluorometer, with translation.

*Primary Examiner*—Alfred E. Smith
*Assistant Examiner*—Carolyn E. Fields

[57] ABSTRACT

A fluorescence microscope with a movable stage has means to stop stage movement when a modified object, such as an abnormal cell, is detected. A beam-splitting plate with an interference coating is provided in the path of radiation from an amplitude modulated irradiation source, which plate is adapted to reflect a short-wave component of fluorescent radiation from an object, accepted by a respective recording channel, and to pass a long-wave component of said fluorescent radiation from the object, accepted by a corresponding recording channel. Outputs of the recording chnnels are connected to the horizontal and vertical deflection plates of a cathode-ray tube so that the slope of the luminous line on the tube screen is proportional to the relationship between the two wavelengths of fluorescent radiation emitted by the object. A movable light detector associated with the screen provides a signal when a modified object is detected, with the signal being used to stop stage movement.

3 Claims, 5 Drawing Figures

APPARATUS FOR INVESTIGATION OF FLUORESCENCE CHARACTERISTICS OF MICROSCOPIC OBJECTS

The invention relates to apparatus for spectral analysis of microscopic objects, and more particularly to apparatus for investigation of fluorescence characteristics of microscopic objects.

1. Field of the Invention

The invention is suitable for use in scientific and applied investigation concerned with biology, chemistry, physics and medicine, including such fields as oncology, hematology, immunology, toxicology, epidemiology, control of medicines action, microbiology and microbiological industry, nature protection, and analysis of powders and microcrystals.

2. Description of the Prior Art

Known in the art is a microspectrofluorimeter intended for investigation and recording of fluorescence characteristics of microscopic objects (cf. an article by Olson R. A., Rapid Scanning Microspectrofluorimeter, in Rev. Scient. Instrum., vol. 31. 1960, p. 844), comprising a fluorescence microscope whose stage carries a microscopic object, and a monochromator whose input slit receives a fluorescent image of the object, enlarged by a microscope. There is a light-sensitive detector after the input slit which is implemented as a photoelectric multiplier converting light signal to electric current passed to the input of a recorder. When the monochromator scanning device operates, the recorder registers the object fluorescence spectrum. It is known that each microscopic object usually produces its own specific spectrum. Therefore, the object can be identified among a set of other objects using its spectral characteristics which represent its physical-chemical properties. When the beginning of a certain process at its earliest stage should be identified, the number of microscopic objects underwent changes is extremely small as compared to the total number of the objects in a sample, a respective ratio being 1:1000 or 1:10,000. To detect a changed microscopic object, it is necessary to record and analyze the fluorescence spectra of hundreds or thousands of microscopic objects, each of them requiring a relatively long period for the purpose. As a result, with the described microspectrofluorimeter, a changed microscopic object is searched for during several tens of hour.

There is a double-beam microfluorimeter (cf. an article by Papayan G. V., Ioffe V. V., Vinogradova V. N., and Barsky I. Ya., Double-beam Pulsed Microspectrofluorimeter with Digital Reading Device, in Cytology, vol. 16, No. 3, 1974, pp. 355–257) intended for recording the intensity of the fluorescence of a microscopic object for two previously selected characteristic intervals of wavelengths in its fluorescence spectrum, but not the entire range of the latter.

The described apparatus comprises a fluorescence microscope whose stage carries a microscopic object which fluoresces under the action of an irradiation source. Introduced into the fluorescent beam from the object is a beam-splitting plate having an interference coating. The plate operates to reflect a short-wave component of the fluorescence radiation accepted by a respective recording channel and to pass a long-wave component thereof into a corresponding recording channel. Each of said channels comprises a serial arrangement of a light filter passing a beam of a narrow-band spectrum, and a photoelectric multiplier whose output is coupled to an amplifier. The outputs of the channel amplifiers are coupled to a digital voltmeter which measures a relationship between the fluorescence intensities of the object for two previously selected characteristic wavelength intervals of the object fluorescence spectrum. These characteristic intervals are so selected that their fluorescence intensities change in accordance with a variation of biological and physical-chemical properties of the object. With this apparatus, the total analysis time for a microscopic object amounts to several hours. Within this period of time, the fluorescence characteristics of hundreds or thousands of microscopic objects of a sample are recorded and compared with one another in order to find out a single object differing from the others in terms of these characteristics and therefore subject to more detailed visual and instrumental examination. Microscopic objects may be as follows: cells of animal or plant tissue; microorganisms; conglomerates of cells; small particles of inorganic nature. The objects may be included in a layer lying on a flat surface such as a glass slide.

SUBJECT OF THE INVENTION

An object of the invention is to provide an apparatus for investigation of fluorescence characteristics of microscopic objects, offering a higher speed of detecting a microscopic object with changed properties to be subject to detailed visual and instrumental examination.

Another object of the invention is to provide an apparatus for investigation of fluorescence characteristics of microscopic objects, capable of performing diagnosis work on very diverse cells, and more speedy and effective diagnosis of diseases encountered in man and animals.

There is provided an apparatus for investigation of fluorescence characteristics of microscopic objects, comprising a fluorescence microscope whose stage carries a microscopic object and a beam-splitting plate adapted to divide a beam of fluorescence radiation excited in the object under the action of an irradiation source so that a short-wave component of said fluorescence radiation is reflected therefrom and passed through a respective recording channel and a long-wave component of said fluorescence radiation is passed directly through a corresponding recording channel, which apparatus comprises, according to the invention, a serial arrangement including a unit to work out a relationship between said components, having its inputs to respective outputs of the channels, a discriminator to detect the level of the value representing the relationship between said components, whose output produces a signal representative of the presence of a changed microscopic object, a control unit, and an electric motor coupled with the microscope stage.

Preferably, with a view to constructing a portable apparatus, the component relationship determination unit should be implemented as a cathode-ray tube having its horizontal deflection plates coupled to the output of one recording channel for one component of the fluorescence radiation of the object, and having its vertical deflection plates coupled to the outputs of the other recording channel for the other component of said fluorescence radiation.

Advantageously, with a view to rearranging easily the apparatus in order that various microscopic objects can be investigated in a broad line of possible applications, the irradiation source should be implemented as a amplitude modulated radiation source and the level discriminator should be implemented as a light-sensitive detector which is fixed in a movable relation to a screen of the cathode-ray tube at a point which determines the boundary representing the presence of changed microscopic objects in the case when that point is brought into intersection with a luminous line characteristic of the relationship between said components of said fluorescence radiation of the object.

Preferably, with a view to simplifying the operation of the apparatus, the level discriminator should comprise, on the screen of the cathode-ray tube, a mask whose configuration determines the boundary representing the presence of changed microscopic objects, and a light-sensitive detector introduced in the path of the light beam passed from the screen.

Advantageously, with a view to obtaining statistical characteristic of all the microscopic objects within a sample, the apparatus should comprise a serial arrangement of a signal separation unit having its inputs coupled to the outputs of said recording channels, and a pulse amplitude analyzer.

Preferably, with a view to determining a relationship between the number of the changed objects to the total number of the objects within a sample, the apparatus should comprise three pulse counters, two of said pulse counters being coupled to the outputs of the recording channels, and a third one of the pulse counters being coupled to the output of the level discriminator.

With the apparatus of the invention, it is possible to considerably increase the speed of detecting a single microscopic object with changed properties among hundreds or thousands of other microscopic objects, not subject to a change, all belonging to a given sample. In addition, the apparatus of the invention features small size and mass, and low manufacturing and operational costs.

DESCRIPTION OF THE DRAWINGS

The invention will now be described, by way of example, with reference to the accompanying drawings in which.

DETAILED DESCRIPTION OF THE INVENTION

Figure 1:
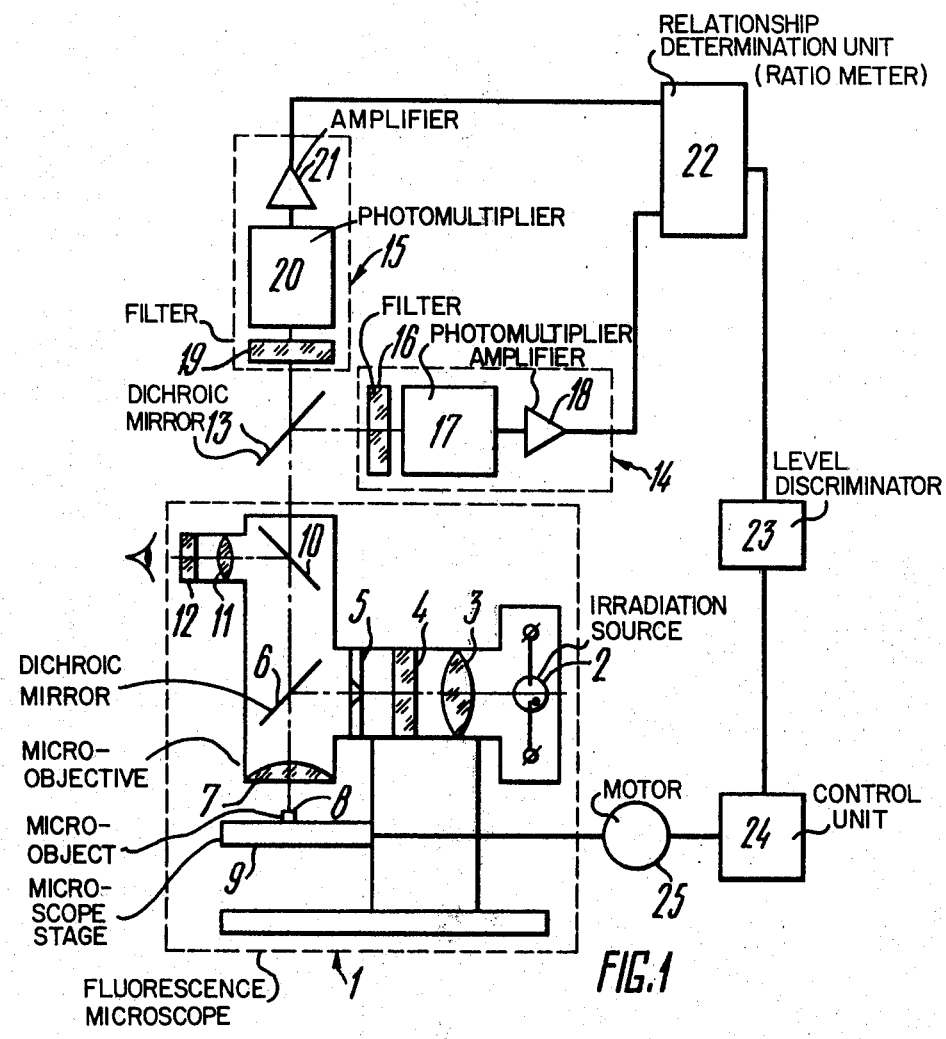
FIG. 1 is a block diagram of an apparatus for investigation of fluorescence characteristics of microscopic objects, according to the invention.

The apparatus of the invention comprises a fluorescence microscope 1 (FIG. 1) which includes an irradiation source 2 whose radiation beam passes through a serial arrangement of a collecting lens 3 to collect the beam, a light filter 4 to select a narrow spectral band from the radiation beam, a field diaphragm 5 to limit the field of vision of the microscope 1, and a beam-splitting plate 6 having an interference coating. The beam reflected from the plate 6 passes through a micro objective 7 and a microscopic object 8 included in a sample carried by a stage 9. The micro objective 7 serves to focus the fluorescence-exciting radiation on to the object 8 and to gather the fluorescent radiation emitted by that object. The beam of the excited fluorescent radiation after passing through the plate 6 impinges on a mirror 10 and then passes through an eyepiece 11 which produces an enlarged fluorescent image of the object 8, having dimensions determined by the field diaphragm 5. There is a light filter 12 between the examiner's eye and the eyepiece 11, said filter rejecting the reflected beam provided by the source 2 and passed through the light filter 4. With the mirror 10 moved out of the path of the beam, a light-splitting plate 13, is exposed to the beam. The plate 13 has an interference coating, and operates to reflect a short-wave component of the fluorescent radiation of the object 8 onto a respective recording channel 14, and to pass a long-wave component of said radiation onto a corresponding channel 15. The channel 14 comprises a narrow-band filter 16 and a photoelectric multiplier 17 which has its output coupled to an input of a variable-gain amplifier 18. The channel 15 comprises a narrow-band filter 19 and a photoelectric multiplier 20 which has its output coupled to an input of a variable-gain amplifier 21.

The outputs of the amplifiers 18,21 are coupled to respective inputs of a ratiometer unit 22 which works out a relationship between said components of said fluorescent radiation of the object 8. The unit 22 has its output coupled to an input of a discriminator 23 which detects the level of the value representing the ratio between the components. The output of the discriminator produces a signal indicative of the presence of a microscopic object 8 with changed properties within the field of vision of the microscope 1, said output being coupled to an input of a control unit 24. An output of the latter is coupled to an electric motor 25 which is connected mechanically with the stage 9.

The ratiometer comprises a cathode-ray tube 26 (FIG. 2) having its horizontal deflection plates 27 coupled to the output of the amplifier 18, and having its vertical deflection plates 28 coupled to the output of the amplifier 21. The level discriminator 23 comprises a light-sensitive detector 29 which is associated with the screen 30 of the cathode-ray tube 26 with the help of a narrow plate 31. The latter has a longitudinal slot 32 along which the detector 29 is moved. The plate 31 is mounted on an axle 33 and is adapted to be rotated about it, together with the detector 29, in parallelism with the screen 30. Thus, a polar-coordinate mechanism including elements 29,30,31,32,33 is adapted to set the detector 29 at a previously selected point on the screen 30. The fluorescent radiation of the microscopic object 8 (FIG. 1) is amplitude-modulated since the irradiation source 2 is amplitude-modulated by virtue of alternating current with which it is supplied.

The fluorescence-exciting radiation can be modulated with the help of a mechanical shutter introduced into the path between the source 2 and the beam-splitting plate 6, with the source 2 fed from a d.c. power supply.

Since the fluorescent radiation of the object 8 is amplitude-modulated, any one of these objects is represented on the screen 30 (FIG. 2) as a luminous line 34 which has the tangent of the angle of inclination relative to the horizontal axis proportional to the value of the relationship between the long-wave and the short-wave components of the fluorescent radiation of the object 8. The objects 8 having different values of said relationship will be represented by luminous lines 34,34′,34″ having different angles of inclination. Thus, the point at which the detector 29 connects the screen 30 determines the boundary, when intersecting with the luminous line 34, of presence of a changed object 8.

The microscopic object 8 can be represented on the screen 30 by luminous line 34 even though the fluorescent radiation of that object is not amplitude-modulated, as it results from the amplitude-modulated irradiation source. When unmodulated radiation is employed to provide excitation of the fluorescent radiation of the object 8, the luminous line 34 on the screen 26 can be obtained by modulating the gain of the amplifiers 18,21 of the photoelectric multipliers 17,20.

Figure 3:
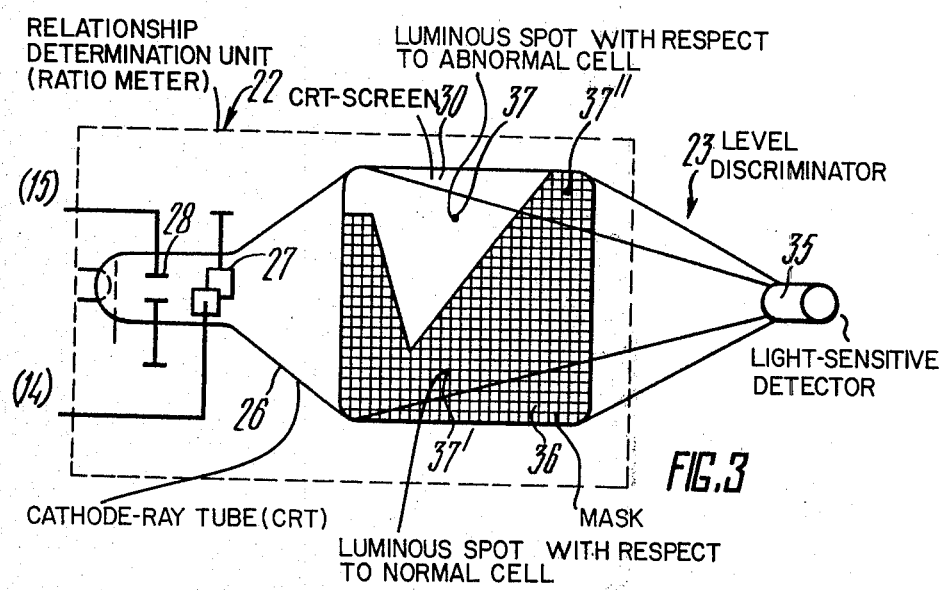
FIG. 3 is another version of a block diagram of the component relationship determination unit and the level discriminator, according to the invention.

To provide for more simple apparatus, the level discriminator 23 may comprise a light-sensitive detector 35 (FIG. 3), introduced into the path of beam from the screen 30, and a mask 36 made of a material which does not pass the radiation characterized by the spectral sensitivity of the detector 35. The mask is mounted on the screen 30. With this embodiment, the irradiation source 2 (FIG. 1) is fed from a d.c. power supply (not shown). Each of the objects 8 is represented on the screen 30 (FIG. 3) by a luminous spot 37 whose coordinates are determined by a relationship of the components of the fluorescent radiation of that object. Thus, the objects having different values of the relationship are represented by luminous spots 37,37′,37″ at different points on the screen 30. In this case, the boundaries of the mask 36 determine the boundary of presence of the objects with changed properties.

A control unit 24 of the apparatus (FIG. 4) comprises a variable-gain amplifier 38 having its input coupled to the output of the level discriminator 23, and having its output coupled to an inverting input of a Schmitt trigger 39. In the apparatus of the invention, the Schmitt trigger 39 is a conventional device of the known type (cf. Analog Integrated Circuits. Devices, Circuits, Systems and Applications. I. A. Connelley (ed.), John Wiley and Sons Publ., New York-London-Sydney-Toronto, 1975). The non-inverting input of the Schmitt trigger 39 is coupled to its output via a resistor 40, and to a slide 42 of a potentiometer 43 via a resistor 41. The potentiometer 43 is connected to a negative pole 44 and positive pole 45 of a power supply (not shown) of the trigger. The slide 42 is coupled to the negative pole 44 via a normally open push button 46 "Stop", and to the positive pole 45 via a normally open push-button 47 "Start". A cut-out 48 is coupled in parallel with the push button 47.

The output of the Schmitt trigger 39 is coupled, via gate 49, to parallel-connected switches 50,51 whose outputs are joined together and are coupled to the electric motor 25. A capacitor 52 is coupled in parallel with the gate 49 having its output coupled to the common point of the power supply of the Schmitt trigger 39 via a variable resistor 53. The output of the switches 50,51 is coupled to an a.f. oscillator 55 and a capacitor 56, which is used as a power supply for the oscillator 55.

To determine a relationship between the number of the changed microscopic objects and the total number of the objects in a sample, the apparatus of the invention comprises a pulse counter 57 coupled via a cut-out 58 to the output of the amplifier 21, a pulse counter 59 coupled via a cut-out 60 to the output of the amplifier 18, and a pulse counter 61 coupled via a cut-out 62 to the output of the level discriminator 23.

To obtain the total statistical characteristic of all the objects in a sample, the apparatus of the invention comprises a serial arrangement of a pulse amplitude analyzer 63 and a signal separation unit 64 having its inputs coupled, via a two-pole cut-out 65, to the outputs of the amplifiers 18,21. The unit 64 utilizes a conventional circuit (cf. a book entitled "Analog and Digital Integrated Circuits", ed. by S. V. Yakubovsky, "Soviet Radio" Publishers, Moscow, 1979, pp. 239–240).

The apparatus of the invention operates in the following manner. A sample including microscopic objects 8 (FIG. 1) is placed on to the stage 9 of the fluorescence microscope 1. The radiation from the source 2, focused by the collecting lens 3 and selected by the light filter 4, impinges on the beam-splitting plate 6 which reflects the fluorescence-exciting radiation by 90° and directs it into the micro objective 7 which is used to focus that radiation in the plane of the sample. As a result, the microscopic objects 8 fluoresce. The fluorescent radiation of the objects is gathered by the micro objective 7, passed through the plate 6, reflected by the mirror 10, and used to form a fluorescent image of the objects 8. The latter is observed by the examiner through the eyepiece 11 and light filter 12 which absorbs the radiation of the source 2. When observing the image, the examiner tries to change the size of the field diaphragm 5 so that the size of the field of vision of the microscope 1 is equal to or greater by severalfold than the size of a single fluorescing microscopic object 8 in the sample. Under these conditions, the examiner brings the mirror 10 out of the path and the fluorescent radiation from the object 8 impinges on the beam-splitting plate 13 which serves to divide it into two components as follows. The short-wave component, reflected by the plate 13, passes through the light filter 16 and impinges on to the cathode of the photoelectric multiplier 17 which converts it to electric signal proportional to its intensity. The output signal of the multiplier 17 is amplified by the amplifier 18 and is applied to a respective input of the component relationship determination unit 22. The long-wave component passes through the plate 13 and the light filter 19 and is incident upon the photocathode of the photoelectric multiplier 20 which converts it to electric signal proportional its intensity. The output signal of the multiplier is amplified by the amplifier 21 and is applied to a respective input of the unit 22. The unit 22 is the cathode-ray tube 26 (FIGS. 2,3) whose horizontal deflection plates 27 accept the output signals of the amplifier 18, and whose vertical deflection plates 28 accept the output signal of the amplifier 21. As a result, the electron beam is deflected from its initial position on the screen 30 to a point whose vertical and horizontal coordinates are related in a proportion to a relationship between the long-wave and short-wave components of the fluorescent radiation of the microscopic object 8.

According to the embodiment of the invention, when an amplitude-modulated irradiation source 2 (FIG. 1) fed from an a.c. power supply is employed. In this case, the electron beam (FIG. 2) is moved at the modulation frequency between the initial position and the point whose horizontal coordinate is proportional the short-wave component and whose vertical coordinate is proportional to the long-wave component. This produces on the screen 30 the luminous line 34 having its tangent of the angle of inclination proportional to the relationship between the long-wave and short-wave components. With the electric motor 25 (FIG. 1) energized, the stage 9 moves in a horizontal plane and the microscopic objects 8 appear, one at a time, in the field of vision of the fluorescence microscope 1, said objects being represented by the luminous lines 34,34',34" on the screen 30. When the object 8 appears which has the value of the relationship between the long-wave and short-wave components exceeding that determined by the position of the detector 29 on the screen 30, respective luminous line 34 intersects the detector 29 which therefore produces electric signal. After that, the control unit 24 (FIG. 1) operates and the electric motor 25 is stopped, since the detected object 8 is in the center of the field of vision of the fluorescence microscope 1. At the same time, the control unit 24 produces a sound signal to notify the examiner that the object 8 is detected which should be subject to a detailed examination. After the fluorescence characteristics of that object have been investigated, the examiner turns on the electric motor 25 and the search procedure is continued.

When moving the detector 29 (FIG. 2) along the slot 32 in the plate 31 and rotating the latter about the axle 33, the examiner brings that detector to a required point on the screen 30, with the result that the boundary surrounding the changed microscopic objects is defined.

Figure 2:
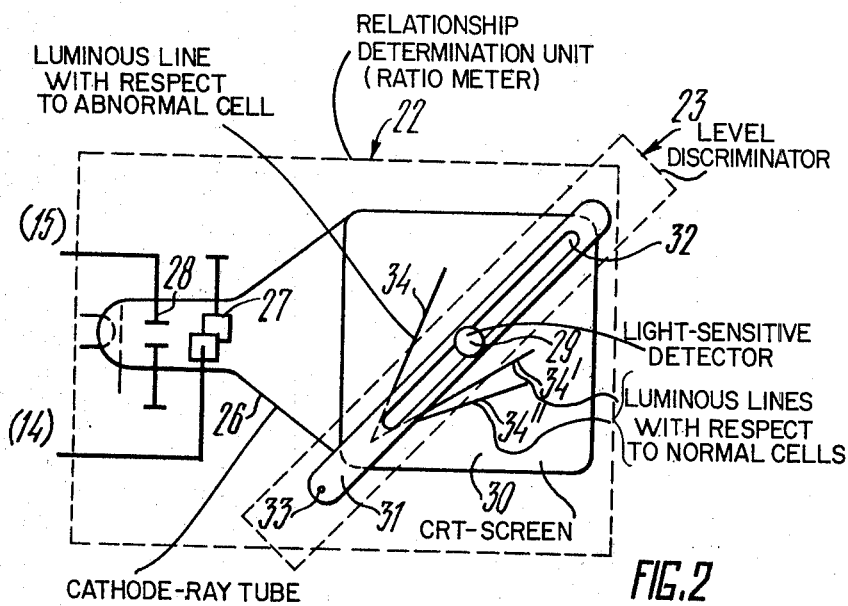
FIG. 2 is a block diagram of a unit to work out a relationship between components of fluorescence radiation of microscopic objects and a discriminator to detect the level of the value representing said relationship, according to the invention.

According to the other embodiment of the apparatus of the invention, when the irradiation source 2 is used which is fed from a d.c. power supply. A microscopic object 8 appearing in the field of vision of the microscope 1, with the electric motor 25 energized, is represented on the screen 30 (FIG. 3) by a luminous spot 37 whose horizontal coordinate is proportional to the short-wave component of the fluorescent radiation of the object and whose vertical coordinate is proportional to the long-wave component. In the case of this embodiment, the level discriminator 23 operates in the following manner. With the electric motor 25 (FIG. 1) energized, microscopic objects 8 appear, one at a time, in the field of vision of the microscope 1, which are represented by luminous spots 37,37',37" (FIG. 3) on the screen 30. When an object 8 appears which has the value of the relationship between the long-wave and short-wave components exceeding that determined by the contours of the mask 36, the luminous spot 37 is generated on that portion of the screen 30 which is not covered by the mask 36. That spot is registered by the detector 35 whose output produces electric signal applied to the input of the control unit 24 (FIG. 1). By changing the contours of the mask 36, the examiner determines any required boundary of presence of the changed microscopic objects 8.

Figure 4:
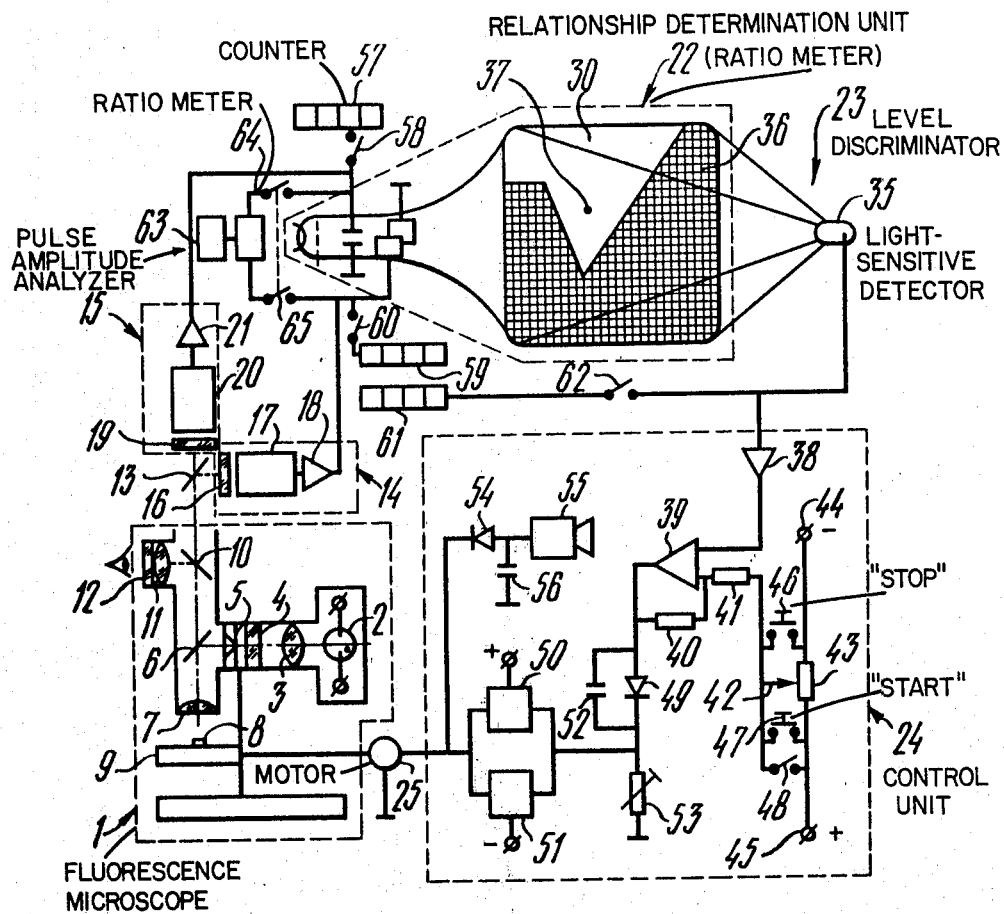
FIG. 4 is another version of an apparatus for investigation of fluorescence characteristics of microscopic objects, according to the invention.

The control unit 34 operates in the following manner (FIG. 4). With the push button 47 "Start" depressed, a positive voltage is applied to the non-inverting input of the Schmitt trigger 39 via the resistor 41. The output of the Schmitt trigger 39 produces a positive voltage which is applied, via the gate 49, to the input of the parallel-connected switches 50, 51. The switch 50 is made conducting and close the supply circuit of the electric motor 25 fed from a positive-polarity cource. The electric motor 25 moves the stage 9 of the microscope 1. When a changed microscopic object 8 appears within the field of vision of the microscope 1, the output of the level discriminator produces electric signal which, after amplification in the amplifier 38, is applied to the inverting input of the Schmitt trigger 39. The latter assumes a state in which its output produces a negative voltage which is applied to the input of the parallel-connected switches 50,51 within a time interval defined by the time constant of an RC circuit comprised of the capacitor 52 and variable resistor 53. The switch 50 is made non-conducting and breaks the supply circuit of the electric motor 25 from the positive polarity source. The switch 51 is made conductive for a time period determined by the value of the capacitor 52 and the value of the variable resistor 53 and closes the supply circuit of the electric motor 25 from the negative polarity source. Thus, the stage 9 moves in reverse direction to compensate for inertia displacement of the object 8 relative to the center of the field of vision of the microscope 1. The negative voltage from the output of the switch 51 is applied, via the gate 54, to the capacitor 56 to charge it. The capacitor 56 is used as a power supply for the a.f. oscillator 55 which operates to notify the examiner that an object is detected which has the value of the relationship between the long-wave and short-wave components exceeding the level preset by the level discriminator 23.

After notification, the examiner introduces the mirror 10 into the path and investigates, through the eyepiece 11 and light filter 12, the morphological features of the detected object 8. After that, he brings the mirror 10 out of the path and checks to see how the relationship between the short-wave and long-wave components is changed under the action of various physical/chemical factors, for instance, ultraviolet rays.

After the detected microscopic object has been investigated, the examiner depresses the push button 47 "Start" and begins to search for microscopic objects 8 with the desired fluorescence characteristics. By depressing the push button 46 "Stop", the examiner can apply, at any given point in time, a negative voltage to the non-inverting input of the Schmitt trigger 39, with the result that the electric motor 25 is stopped. The slide 42 of the potentiometer 43 is used to select the operating mode of the Schmitt trigger 39. The cut-out 48 interlocks the push button 47 "Start" for the apparatus adjustment procedure. By operating the cut-out 58 to couple the pulse counter 57 to the output of the recording channel 15 or connecting the pulse counter 59 to the output of the channel 14 with the help of the cut-out 60, the examiner obtains data on the total number of the fluorescent objects 8 in the sample. By connecting the pulse counter 61 to the output of the level discriminator 23, the examiner obtains data on the number of the changed objects 8 in the sample. Using the data provided by the counter 57 or 59 and the counter 61 as well, it is possible to determine the content of the changed objects 8 in the sample.

With the inputs of the signal separation unit 64 coupled to the outputs of the channels 14,15 with the help of the two-pole cut-out 65, the output of that unit produces a signal representing the value of the relationship of the long-wave and short-wave components of the fluorescent radiation of the object 8. This signal is applied to the input of the amplitude pulse analyzer 63 which generates a histogram depicting the amplitude distribution of the values representing the relationships between the long-wave and short-wave components for all the luminescent objects in the sample.

The Example given below illustrate possible applications of the apparatus of the invention.

EXAMPLE 1.

Medical Diagnostics

Smears of blood, bone marrow, ascites, mucosa biopsy specimens, impressions of biopsy material, tissue sections on glass slide are fixed with Carnois liquid or ethanol-acetone solution (1:1) for 4 to 10 minutes and are held in citrate-phosphate buffer having pH of 4.0-4.6 for 4 to 6 minutes, and are stained in acridine orange having a concentration of $5 \cdot 10^{-5}$ to $10^{-4}$ using citrate-phosphate buffer with pH of 4.0-4.2 for 8-12 minutes at 18°-20° C. The stained preparations are washed with the same buffer solution or in distilled water, covered by a cover glass, and are placed on the stage 9.

Use is made of the beam-splitting plate 13 (FIG. 1) which reflects the green region of the spectrum (500-580 nm) and passes the red region of the spectrum (600-700 nm), and light filters 4,16,19 having maximum pass bands at 436,530, and 640 nm, respectively. The pulse counters 59,61 are energized.

The characteristic symptom is a relationship of the intensities of the red component (640 nm) of the fluorescent radiation of the cell, $I_{640}$, and the green component (530 nm) of the fluorescent radiation of the cell, $I_{530}$, said relationship being proportional to a relationship between the amount of single-spiral nucleic acids ($NA_1$) and the amount of double-spiral nucleic acids ($NA_2$) in the cell $$\alpha = I_{640}/I_{530} = A \cdot NA_1/NA_2 \qquad (1)$$

where A is a coefficient of proportionality. By setting a certain operating level of the level discriminator 23, the examiner energizes the electric motor 25 of the stage 9 and depresses the push button 47 "Start" to detect quickly the cell with changed properties which has its characteristic $\alpha$ exceeding the preset level of the discriminator 23. After a sound signal is heard, the examiner brings the mirror 10 into the path and utilizes the eyepiece 11 to investigate the morphological characteristics of the detected cell with changed properties.

Figure 5:
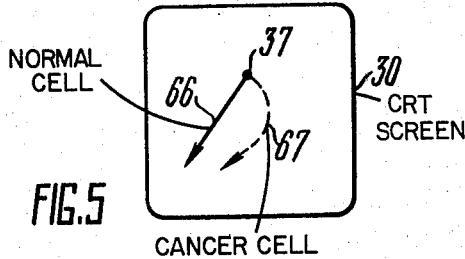
FIG. 5 shows a path of movement of a luminous spot produced on a screen of a cathode-ray tube in case when a cell with changed properties is a normal one (solid line) or a cancerated one (dotted line).

With the morphological investigation completed, the examiner brings the mirror 10 out of the path and investigates the process of photodecomposition of the dye in the detected cell. If this process takes place in a manner that the path of movement 66 (FIG. 5) of the luminous spot 37 on the screen 30 of the cathode-ray tube 26 is directed along the line connecting the coordinate origin and the initial point characteristic of the cell, then the latter belongs to a family of normal undifferentiated cells and an increased value of $\alpha$ is resulted from its higher synthetic activity.

Note that the presence of blast cells in bone marrow is a normal condition. If, however, a cell is found among the detected ones, having an increased value of $\alpha$ and belonging to the other cytological preparations mentioned-above, in which cell the photodecomposition of the dye, under the action of the irradiation source 2, occurs in a manner that a decrease in the intensity of the red component is accompanied by an increase in the intensity of the green component and the path of movement 67 of the luminous spot 37 on the screen 30 has an important component perpendicular to the line connecting the coordinate origin with the initial point 37, then the cell is of undifferentiated or differentiated cancer nature, which acknowledges that a serious pathology is present in the organism. If the photodecomposition of the above type is characteristic of segmental-nuclear granulocite of the peripheral blood, easily determined by the morphological symptoms with the help of the eyepiece 11, this indicates one of the forms of the systemic lupus.

After the detected cell with changed properties has been investigated visually and instrumentally, the examiner depresses the push button 47 "Start" and the search procedure is continued. With the preparation analyzed, the examiner obtains data on the total number of the nuclear cells in the preparation (the pulse counter 59), on the number of the changed cells in the preparation (the pulse counter 61), and on the degree of change of the cells, if any, at morphological and molecular levels.

EXAMPLE 2.

Immunology

The organism cells are incubated with antibodies labeled by fluorescent dyes, for example, 4-acetamido, 4'-isothiocyanostilbene-2,2'-disulfonic acid, using techniques intended for the given immune reaction. After that, a solution of ethidium bromide of a concentration of $10^{-4}$-$10^{-5}$ g/ml (2,7-diamino-10-ethyl-9-phenyl-phenantridium bromide) is added, the preparation is covered by a cover glass and is placed, after 1 to 8 minutes, on the stage 9.

Use is made of the beam-splitting plate 13 (FIG. 1) which reflects in the blue portion of the spectrum (400-500 nm) and passes in the red portion of the spectrum (580-700 nm), and light filters 4,16,19 having pass band maxima at 365,460 and 610 nm, respectively. The pulse counters 57,61 are energized.

The characteristic symptom is a relationship between the intensities of the fluorescence for the blue, $I_{460\ nm}$, and red, $I_{610\ nm}$, spectrum regions, which relationship being characteristic of a relationship between the intensity of immuno-fluorescent label, L, and the total content of nucleic acids, NA, in the given cell $$\alpha = I_{460}/I_{610} = A \cdot L/NC, \qquad (2)$$

where A is a coefficient of proportionality.

With the desired level of the discriminator 23 preset, the examiner depresses the push button 47 "Start" to energize the electric motor 25 and quickly determines the cells of higher immune activity, if any, in the preparation. The detected cells are examined morphologically using the eyepiece 11. With the analysis procedure complete, the examiner obtains data on the total amount of the cells in the sample (the pulse counter 57), on the number of the cells with higher immune activity (the pulse counter 61), and on the morphology of these cells (the eyepiece 11).

EXAMPLE 3.

Microbiology

Added to a suspension of Gram-negative microorganisms-producers are water solutions of 1-anilino-naphthaleno-8-sulfonate, having a concentration of $10^{-4}$ g/ml, and ethidium bromide, having a concentration of $10^{-5}$ g/ml. The prepared mixture is placed on a glass slide, covered with a cover glass and put of the stage 9.

Use is made of the beam-splitting plate 13 which reflects in the blue (400-520 nm) and passes in the red (580-700 nm) spectral regions, and light filters 4,16,19 with pass band maxima at 365, 490, and 610 nm, respectively.

The characteristic symptom is a relationship between the fluorescence intensities for the red, $I_{610}$, and blue, $I_{490}$, spectral regions $$\alpha = I_{610}/I_{490}, \quad (3)$$

which is characteristic of the degree of damage to the cell.

With the desired level of the discriminator 23 preset, the examiner depresses the push button 47 "Start" and quickly determines the cells with preset or higher degree of damage. The cells are then subject to morphological analysis with the help of the eyepiece 11.

EXAMPLE 4.

Cell Energetics

A suspension of living cells or an impression of biopsy material is applied on to a glass slide, covered with a cover glass, and placed on the stage 9.

Use is made of the beam-splitting plate 13 which reflects in the blue (400–490 nm) and passes in the green (500–600 nm) spectral regions, and light filters 4,16,19 having pass band maxima at 365, 470, and 530 nm, respectively.

The characteristic symptom is a relationship between the fluorescence intensities of the oxidized flavoproteins at 530 nm and the reduced pyridine nucleotides at 470 nm $$\alpha = I_{530}/I_{470}, \quad (4)$$

which is characteristic of the energetic activity of the cell.

With the desired level of the discriminator 23 preset, the examiner depresses the push button 47 "Start", quickly determines the cells with higher energetic activity and investigates them with the help of the eyepiece 11.

EXAMPLE 5.

Biomonitoring of Microphytoplancton

A drop of water from a water body is applied on to a glass slide, covered with a cover glass and placed on the stage 9.

Use is made of the beam-splitting plate 13 which reflects in the yellow-orange (560–660 nm) and passes in the red (670–750 nm) spectral regions, and light filters 4,16,19 having pass band maxima at 436, 660, and 680 nm. The pulse counters 57,61 are energized.

The characteristic symptom of the cell a relationship between the fluorescence intensities of allophycocyanin (660 nm) and chlorophyll (680 nm)

$$\alpha = I_{660}/I_{680}, \quad (5)$$

which is characteristic of the age of the cells of blue-green alga.

With the desirable level of the discriminator 23 preset, the examiner detects cells of blue-green alga which are in the stationary phase of development. At the same time, he obtains data on the relationship between the number of the cells of blue-green alga in the stationary phase of development (the pulse counter 61) to the total number of microphytoplancton (the pulse counter 57).

The preparation is subject to complete irradiation of ultraviolet rays at 365 nm for 5–10 minutes. After that, the preparation is analyzed to determine the relationship between the total number of the cells of blue-green alga (the pulse counter 61) and the total number of the cells of microphytoplancton (the pulse counter 57).

For all the described Examples, the apparatus of the invention is advantageous in that it can analyze, for example, according to Example 1, 100 to 200 preparations of human tissues within one working day in order to detect differentiated cancer cells in the case when 1 to 2 pathological cells are available for 1000 to 10,000 normal cells. The diagnosis of undifferentiated condition of a cancer cell is performed with a higher degree of accuracy since specific physical/chemical properties of the cell (dye photodecomposition) are utilized in addition to conventional morphological visual examination. Since the apparatus of the invention offers simple design features, its manufacture and operational costs are decreased by a factor of 7 to 10, as compared to the known automatic devices which utilize morphological symptoms in detecting cells which seem to be pathological.

What is claimed is:

1. Apparatus for investigation of fluorescence characteristics of microscopic objects and for distinguishing between modified and unmodified objects, comprising:

a fluorescence microscope having an amplitude modulated irradiation source and a movable stage which carries a microscopic object emitting fluorescent radiation under the action of said irradiation source;

a beam-splitting plate having an interference coating, adapted to reflect a short-wave component of said fluorescent radiation and to pass a long-wave component of said fluorescent radiation, said plate being located in the path of said fluorescent radiation;

a first recording channel to register a respective component of said fluorescent radiation from said microscopic object said channel being located in the path of the fluorescent radiation reflected from said beam-splitting plate, said channel having an output;

a second recording channel to register a corresponding component of said fluorescent radiation, said channel being located in the path of said fluorescent radiation passed by said beam-splitting plate, said channel having an output;

means for determining a relationship between said components, said means comprising a cathode-ray tube having its horizontal deflection plates coupled to the output of said first recording channel, and having its vertical deflection plates coupled to the output of said second recording channel;

a level discriminator comprising a light-sensitive detector having an input which is connected to the screen of said cathode-ray tube, and an output forming a signal which is indicative of the presence of a modified microscopic object;

said light-sensitive detector being fixed on the screen of said cathode-ray tube in a movable relation to said screen at a point which determines the boundary of presence of modified microscopic objects when the detector is intersected with a luminous line corresponding to said relationship between said components of said fluorescent radiation from the object;

a control unit having an input and an output, whose input is coupled to the output of said light-sensitive detector;

means for stopping said stage in compliance with a signal from said control unit when a modified object is detected, said means comprising an electric motor having an input coupled to the output of said control unit and an output coupled to said stage.

2. The apparatus as claimed in claim 1, including;

a signal separation unit having a first input, a second input and an output, said first input being coupled to said output of said first recording channel, and said second input being coupled to said output of said second recording channel and;

a pulse amplitude analyzer having an input coupled to said output of said signal separation unit.

3. The apparatus as claimed in claim 2, including:

a first pulse counter having an input coupled to said output of said first recording channel;

a second pulse counter having an input coupled to said output of said second recording channel;

a third pulse counter having an input coupled to said level discriminator.

* * * * *